United States Patent
Drent et al.

(10) Patent No.: US 6,737,542 B1
(45) Date of Patent: May 18, 2004

(54) PROCESS FOR THE CARBONYLATION OF CONJUGATED DIENES

(75) Inventors: Eit Drent, Amsterdam (NL); Willem Wabe Jager, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/937,122

(22) PCT Filed: Mar. 16, 2000

(86) PCT No.: PCT/EP00/02375

§ 371 (c)(1),
(2), (4) Date: Sep. 20, 2001

(87) PCT Pub. No.: WO00/56695

PCT Pub. Date: Sep. 28, 2000

(30) Foreign Application Priority Data

Mar. 22, 1999 (EP) ............................................ 99302202

(51) Int. Cl.$^7$ ............................................... C07C 67/36

(52) U.S. Cl. ........................ 560/207; 560/114; 560/204; 560/233

(58) Field of Search ................................ 560/207, 114, 560/204, 233; 502/202

(56) References Cited

U.S. PATENT DOCUMENTS

| | | | | |
|---|---|---|---|---|
| 4,433,164 A | * | 2/1984 | Jenck | 560/207 |
| 4,861,912 A | * | 8/1989 | Drent et al. | 560/204 |
| 5,028,734 A | * | 7/1991 | Drent | 560/207 |
| 5,087,735 A | * | 2/1992 | Denis | 560/204 |
| 5,495,041 A | * | 2/1996 | Sielcken et al. | 560/207 |
| 5,672,732 A | * | 9/1997 | Agterberg et al. | 560/207 |
| 6,010,975 A | * | 1/2000 | Tsai | 502/155 |
| 6,232,262 B1 | * | 5/2001 | Sielcken et al. | 502/162 |

* cited by examiner

Primary Examiner—Paul J. Killos
Assistant Examiner—Hector M. Reyes

(57) ABSTRACT

The present invention relates to a process for the carbonylation of conjugated dienes, whereby a conjugated diene is reacted with carbon monoxide and a hydroxyl group containing compound in the presence of a catalyst system including: (a) a source of palladium cations, (b) a phosphorus-containing ligand, (c) a source of anions, wherein the phosphorus-containing ligand is a ligand having the general formula (I): $X^1$—R—$X^2$ wherein $X^1$ and $X^2$ represent a substituted or non-substituted cyclic group with at least 5 ring atoms, of which one is a phosphorus atom, and R represents a bivalent organic bridging group, connecting both phosphorus atoms, containing from 1 to 4 atoms in the bridge, whereby the carbonylation process can be performed batch wise, semi-continuously or continuously.

20 Claims, No Drawings

PROCESS FOR THE CARBONYLATION OF CONJUGATED DIENES

The present invention relates to a process for the carbonylation of conjugated dienes, whereby a conjugated diene is reacted with carbon monoxide and a hydroxyl group containing compound in the presence of a catalyst system including a source of palladium cations, a phosphorus-containing ligand and a source of anions. In particular it relates to the preparation of alkyl pentenoates and/or adipates from 1,3-butadiene and derivatives thereof.

U.S. Patent publication No. 5,495,041 describes a process for the preparation of a pentenoate ester by carbonylation of butadiene in the presence of carbon monoxide, alcohol and a catalyst system comprising palladium, pentenoic acid and a phosphorus-containing ligand. The phosphorus-containing ligand can be a monodentate or multidentate phosphorus-containing ligand or a mixture thereof. Preferably a monodentate phosphorus-containing ligand is used to obtain a high selectivity. The examples disclose the use of 1,4-bis(diphenyl-phoshino) butane and triphenyl phosphine as phosphorus-containing ligands. The molar ratio of butadiene to palladium is according to this publication, preferably less than 20:1. A disadvantage is that this catalyst system has only a moderate activity.

European patent publication No. 0198521 describes a process for preparing carboxylic di-esters, or carboxylic di-acids by the reaction of a conjugated diene with carbon monoxide and an alkanol or water in the presence of an aprotic solvent and a dissolved catalyst system comprising a divalent palladium compound, a triaryl phosphine and hydrogen chloride. The catalyst system may further comprise a bidentate phosphorus-containing ligand, i.e. a bis(diaryl-phoshino)alkane. In its examples it is illustrated that the process can also be used for the preparation of mono-esters. The conversion of 1,3-butadiene to carboxylic diesters or to mono-esters is performed in one step. Because, at least one mole of hydrogen chloride per atom of trivalent phosphorus present in the catalytic system is considered necessary, supplementary, cost-increasing measures are required to avoid corrosion. Examples disclose that the molar ratio of conjugated diene to palladium is about 115:1.

Object of the present invention, is to provide an improved process in terms of catalyst activity for carbonylation of conjugated dienes.

An improved process has now been found for the selective conversion of conjugated dienes such as 1,3-butadiene, with a high conversion rate, in the presence of a specific catalyst system.

The present invention therefore provides a process for the carbonylation of conjugated dienes, whereby a conjugated diene is reacted with carbon monoxide and a hydroxyl group containing compound in the presence of a catalyst system based on:

(a) a source of palladium cations,
(b) a phosphorus-containing ligand
(c) a source of anions, wherein the phosphorus-containing ligand is a ligand having the general formula I

$$X^1—R—X^2 \quad \quad (I)$$

wherein $X^1$ and $X^2$ represent a substituted or non-substituted cyclic group with at least 5 ring atoms, of which one is a phosphorus atom, and R represents a bivalent organic bridging group, connecting both phosphorus atoms, containing from 1 to 4 atoms in the bridge.

This specific catalyst system has an unexpectedly high activity, which allows for molar ratios well over 200:1 and suitably well over 300:1 of conjugated diene to palladium to be used, whilst still obtaining high selectivities to the desired product(s). High conversion rates are achieved without the necessity of the presence of halides, thus allowing cheaper types of steel for the reactor installations. A further advantage is that in one step simultaneously both mono-esters and di-esters, and in particular mono-esters and di-esters of butadiene, such as methyl-pentenoate and dimethyl adipate, can be prepared.

A catalyst system comprising palladium cations, a carboxylic acid and 1,2-bis(cyclooctylenephosphino)ethane as the phosphorus-containing ligand is described in PCT patent publication 9703943 for the carbonylation of ethene.

However, the process of the present invention is specifically directed to the carbonylation of conjugated dienes, which show specific reaction characteristics when compared to olefins in general. Conjugated dienes contain at least two conjugated double bonds in the molecule. By conjugation is meant that the location of the π-orbital is such that it can overlap other orbitals in the molecule. Thus, the effects of compounds with at least two conjugated double bonds are often different in several ways from those of compounds with no conjugated bonds. It is generally acknowledged that the carbonylation of conjugated dienes comprises more difficulties than that of a mono-olefin. For example, in European patent publication No. 0495548, relating to the carbonylation of olefins with a catalyst system obtainable by combining a group VIII metal with a bidentate phosphorus-containing ligand, i.e. a bis(di(tertiary alkyl)-phoshino) alkane, it is stated that diolefins with more than one unsaturated double bond may be used, however, in particular those wherein the double bonds are non-conjugated.

The process of the present invention can advantageously be used to prepare mono-esters and/or diesters in one step. By optimising reaction conditions such as the residence time, the pressure, the temperature, the amount of hydroxyl group containing compound, the source of anions and specific type of ligand, the process can be made more selective by the skilled person to either mono-esters or diesters as will be described in more detail below.

Preferred hydroxyl group containing compounds in the process of the invention are alkanols with 1 to 20, more preferably with 1 to 6 carbon atoms per molecule and alkanediols with 2–20, more preferably 2 to 6 carbon atoms per molecule. Suitable alkanols in the process of the invention include methanol, ethanol, propanol, iso-propanol, butanol, iso-butanol, tert.butanol, pentanol, hexanol, cyclohexanol and phenol. Preferably methanol or ethanol is used as a hydroxyl group containing compound. Methanol is especially preferred as a hydroxyl group containing compound.

The conjugated diene preferably is a conjugated diene having from 4 to 20, more preferably from 4 to 8 carbon atoms per molecule. The conjugated diene can be substituted or non-substituted. Most preferably, the conjugated diene is non-substituted 1,3-butadiene.

For example when methanol is used as a hydroxyl group containing compound in the carboxylation process of 1,3-butadiene enables the production of methyl-pentenoate and/or dimethyl adipate and preferably both. Dimethyl adipate is an intermediate compound in the preparation of adipic acid, an intermediate compound to prepare Nylon 6,6. Methyl-pentenoate is an important intermediate in the production process of ϵ-caprolactam. For the preparation of ϵ-caprolactam, methyl-pentenoate is hydroformylated to methyl formylvalerate, which after reductive amination and cyclisation forms ϵ-caprolactam. ϵ-Caprolactam is a starting material in the manufacture of Nylon 6 fibres or engineering plastics. Hydroformylation, reductive amination and cyclisation can be performed in any manner known to a person skilled in the art. Suitable processes are given in PCT application No. 95/0625 and Japanese patent application No. 25351/66A.

The process of the present invention is therefore particularly advantageous when there is a need to supply both methyl-pentenoate, as an intermediate for preparation of Nylon 6, as well as dimethyl adipate, as an intermediate for the preparation of Nylon 6,6. The amount prepared of each intermediate can be varied, in proportion to the commercial need, by varying the reaction conditions.

The person with average skill in the art will further realise that the process of the present invention can also be used to prepare carboxylic mono-acids and/or carboxylic diacids. Carboxylic mono-acids and/or carboxylic diacids are prepared by reacting conjugated dienes with carbon monoxide and using water as a hydroxyl group containing compound. In this case, the carbonylation product, i.e. the carboxylic acid or di-acid can be used as the source of anions.

A suitable source for palladium cations of component (a) are its salts. Preferably, a salt of a carboxylic acid is used, suitably a carboxylic acid with up to 10 carbon atoms, such as salts of acetic acid, propionic acid and butanoic acid, or salts of substituted carboxylic acids such as trichloroacetic acid and trifluoroacetic acid. A very suitable source is palladium(II) acetate.

The phosphorus-containing ligand of component (b) of the general formula I

$$X^1—R—X^2 \qquad (I)$$

represents a bidentate ligand wherein $X^1$ and $X^2$ represent a substituted or non-substituted cyclic group with at least 5 ring atoms, of which one is a phosphorus atom, and R represents a bivalent organic bridging group, connecting both phosphorus atoms, containing from 1 to 4 atoms in the bridge.

By "a bridge" is understood the shortest connection between both phosphorus atoms. Preferably, the bridging group R represents an alkylene group containing from 1 to 4 carbons atoms in the bridge, but it may also comprise a carbon chain, interrupted by a hetero atom, such as nitrogen, sulphur, silicon or oxygen atom. The alkylene group can be substituted or non-substituted or can form part of a aliphatic or aromatic ring structure. Most preferably, R represents a substituted or non-substituted ethylene or propylene group, connecting both phosphorus atoms by the first and the second or the third carbon atom, such as a 1,2-ethylene, a 1,2-propylene or a 1,3-propylene group.

$X^1$ and $X^2$ represent a substituted or non-substituted cyclic group with at least 5 ring atoms, of which one is a phosphorus atom, and preferably with from 6 to 10 ring atoms. More preferably $X^1$ and $X^2$ represent a substituted or non-substituted cyclic group with 9 ring atoms, of which one is a phosphorus atom. By "a cyclic group" is understood a monocyclic or polycyclic group. Preferred cyclic groups are bicyclic groups. Particularly preferred is a substituted or non-substituted bicyclononyl group wherein one carbon atom is replaced by the phosphorus atom, i.e. a 9-phosphabicyclononyl group. The 9-phosphabicyclononyl group can have several isomeric structures. For the purpose of the invention the [3,3,1] and [4,2,1] isomers are preferred. Suitably $X^1$ and $X^2$ are substituted or non-substituted [3,3,1] or [4,2,1] 9-phosphabicyclononyl groups. The two 9-phosphabicyclononyl groups can have both the same or each a different isomeric structure.

One or both of the phosphabicyclononyl rings can be substituted with one or more suitable hydrocarbyl groups containing carbon atoms and/or hetero atoms. Suitable substituents include groups containing hetero-atoms such as halides, sulphur, phosphor, oxygen and nitrogen. Examples of such groups include chloride, bromide, iodide, thiol, and groups of the general formula $R^2$—O—, —S—$R^2$, —CO—$R^2$, —NH$_2$, —NHR$^2$, —NR$^2$R$^3$, —CO—NR$^2$R$^3$, —OH, —PO$_4$, —NO$_2$, —NOH, —CO, —SO$_2$, —SOH, in which $R^2$ and $R^3$, independently, represent hydrocarbyl groups like methyl, ethyl, propyl and isopropyl. Groups containing carbon-atoms include straight-chain or branched saturated or non-saturated carbon containing groups. If a phosphabicyclononyl ring is substituted it is preferably substituted with a carbon containing group. Such a carbon containing group can, however, contain additional hetero atoms, such as halides, sulphur, oxygen and nitrogen or hetero-groups as described hereinbefore. Preferably, substituted phosphabicyclononyl rings are substituted with alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used. The substituted phosphabicyclononyl ring can be mono- or poly-substituted and is preferably di-substituted. Most preferably the phosphabicyclononyl ring is substituted with two methyl groups. The phosphabicyclononyl ring can be substituted at all carbon atoms of the ring. However, the use of rings with substituents on certain carbon atoms can be more beneficial. Suitably, rings are used with substituents on two carbon atoms, suitably carbon atom 1, 2, 8 and carbon atom 4, 5 or 6.

Suitable phosphorus-containing ligands of formula (I) thus include substituted or non-substituted:

symmetric or asymmetric [3,3,1] or [4,2,1] isomers of 1,3-P,P'bis (9-phosphabicyclononyl) propane;

symmetric or asymmetric [3,3,1] or [4,2,1] isomers of 1,2-P,P'bis(9-phosphabicyclononyl)propane;

symmetric or asymmetric [3,3,1] or [4,2,1] isomer of 1,2-P,P'bis(9-phosphabicyclononyl)ethane; and mixtures of above mentioned compounds.

The selectivity of the process to either mono-esters or diesters can be partly regulated by the phosphorus-containing ligand used. Diesters are most suitably prepared with a catalyst system wherein the phosphorus-containing ligands of formula (I) are non-substituted. For the preparation of mono-esters one or both of the phosphabicyclononyl rings of the abovementioned phosphorus-containing ligands is preferably substituted. Suitable substituted diphosphines for the preparation of mono-esters include, symmetric or asymmetric [3,3,1] or [4,2,1] isomers of 1,2-P,P'bis(1,5-dimethyl, 9-phospha bicyclononyl)ethane and mixtures thereof or symmetric or asymmetric [3,3,1] or [4,2,1] isomers of 1,3-P,P'bis(1,5-dimethyl, 9-phosphabicyclononyl) propane and mixtures thereof or symmetric or asymmetric [3,3,1] or [4,2,1] isomers of 1,2-P,P'bis(1,5-dimethyl 9-phosphabicyclononyl)propane and mixtures thereof, or a combination of above mentioned diphosphines.

The above mentioned phosphorus-containing ligands can be prepared by methods known in the art, such as for example the method known from British patent publication GB-1127965. Suitably the phosphorus-containing ligands can be prepared by refluxing the phosphabicyclononane hydride with 1,2-dibromoethane in acetonitril. After neutralisation with sodium hydroxide the bis (9-phosphabicyclononyl)ethane can be isolated. The phosphabicyclononane hydride may conveniently be prepared as described by Elsner et al. (Chem. Abstr. 1978, vol. 89, 180154x). Substituted phosphabicyclononane hydride is conveniently prepared by using substituted cyclooctadienes in the hereinbefore mentioned process described by Elsner et al.

The source of anions of component (c) can essentially be any salt or acid or a combination of salt and acid.

Preferably an acid is used. A wide range of acids can be used, including halide acids, such as hydrochloric acid and hydrobromic acid, mineral acids, such as sulphuric acid, nitric acid and phosphoric acid, and organic acids, such as acetylacetonic acids, sulphonic acids and carboxylic acids. Preferably, a protonic acid is used, such as sulphuric acid, phosphoric acid and carboxylic acids. More preferably a carboxylic acid is used. When a protonic acid, preferably a carboxylic acid, is used, preferably an acid with a pKa value >1 in aqueous solution at a temperature of 25° C. is used. Especially suitable acids are benzoic acids. Such a benzoic acid can be substituted. Suitable substituents include halide groups, hydrocarbyl groups, carboxy groups and alkoxy groups. Especially preferred benzoic acids include those substituted with methyl or methoxy groups, such as 2,6-dimethoxybenzoic acid and 2,4,6-trimethylbenzoic acid.

Suitable salts include any salts formed with inert substantially non-coordinating cations, such as sodium or potassium. Suitable salts include the salts of the abovementioned acids.

In a preferred embodiment the source of anions is the same as the source of palladium cations in using a palladium salt.

In another preferred embodiment, the source of anions is the carboxylic acid, which results from the carbonylation reaction of the conjugated diene with carbon monoxide and water or obtainable by hydrolysis of the ester product, thus the acid derivative of the ester product to be prepared. For example, if the conjugated diene is 1,3-butadiene, component (c) might conveniently be pentenoic acid, pentenoic acid being the product of the carbonylation of 1,3-butadiene with carbon monoxide and water. Component (c) of the catalyst system might thus be different for each conjugated diene used. The advantage is that any reaction of the component (c) with the hydroxyl group containing compound results in the same product as obtained by the carbonylation of the conjugated diene with that hydroxyl group containing compound.

The source of anions can furthermore be any combination of hereinbefore mentioned acids and salts. The molar ratio of acid and salt can vary between wide limits and suitably lies in the range of 100:1 to 1:100, more suitably in the range of 100:1 to 1:1.

The selectivity of the process to either mono-esters or diesters can be partly regulated by the source of anions used. Depending on the other reaction conditions, the preparation of diesters can, for example, be favoured by the use of an alkoxy substituted benzoic acid or salt thereof, whereas the preparation of mono-esters can for example be favoured by a carboxylic acid as pentenoic acid. In a suitable embodiment for the preparation of diesters, an carboxylic acid is combined with an under the reaction conditions substantially less-coordinating salt.

The selectivity of the process to either mono-esters or diesters can further be regulated by means of residence time. Residence time in the reaction vessel can vary with other factors such as the specific ligand used, the source of anions used and the pressure. Optimal residence times in the reaction vessel might further be determined dependent of other factors known to one skilled in the art such as the catalyst concentration used and the size of the reaction vessel. Residence time can be very short, even in the range of seconds, dependent of a continuous, semi-continuous or batch-wise process is being used. For a batch-wise process, suitably the residence times are in the range to 48 hours, more suitably in the range of 10 minutes to 15 hours. Generally a residence time near the upper limit of this range favours the preparation of diesters and a residence time near the lower limit of this range favours the preparation of mono-esters.

The selectivity of the process to either mono-esters or diesters can also be influenced by means of pressure. Reaction pressures may be atmospheric or superatmospheric. In particular the pressures are conveniently ranging from 1 to 100 bar, preferably 1–30 bar.

The use of a low pressure favours the preparation of diesters, while the use of a higher pressure favours the preparation of mono-esters. The pressure used for a specific set of reactants and required product may be determined by simple experimentation. The ratio of mono-esters and diesters prepared at a certain pressure can further be regulated by other reaction conditions as mentioned herein.

Carbon monoxide partial pressures in the range of 1–65 bar are preferred. In the process according to the present invention, the carbon monoxide can be used in its pure form or diluted with an inert gas such as nitrogen, carbon dioxide or noble gases such as argon.

The molar ratio of conjugated dienes, in particular butadiene, and hydroxyl group containing compound can vary between wide limits and suitably lies in the range of 1:0.1 to 1:10, more suitably from 1:1 to 1:6. Generally a molar ratio near the lower limit of this range favours the preparation of diesters and a molar ratio near the higher limit of this range favours the preparation of mono-esters. The amount of hydroxyl group containing compound to be used for the preparation of mono-esters and/or di-esters needs to be optimised in relation to other hereinbefore described factors that influence the ratio between mono-esters and diesters prepared, such as residence time and pressure.

The selectivity of the process to a certain compound, expressed in a percentage, is defined as:

$$\frac{a}{b} \times 100\%$$

wherein "a" is the amount of conjugated diene that has been converted into that certain compound and "b" the total amount of converted conjugated diene.

It will be clear that a very high selectivity for the conversion of the conjugated diene in the mono-ester or derivatives thereof is obtained at the cost of the conversion in the diester or derivatives thereof.

The carbonylation process can be performed batchwise, semi-continuously or continuously. Preferably a continuous manner of operation is used. The use of a continuous manner of operation conveniently allows for even higher molar ratios of conjugated diene to palladium and lower residence times to be used, when compared to the use of a batchwise manner of operation.

The ratio of moles of phosphorus-containing ligand, i.e. catalyst component (b), per mole of palladium cation, i.e. catalyst component (a), ranges from 0.5 to 10, preferably from 1 to 2.

The quantity of, for instance in-situ prepared, carboxylic acid used in the carbonylation reaction may vary within wide ranges. Preferably, the amount of acid ranges from 1 mole to 1000 mole of acid per mole of palladium cation.

The process of the present invention can be used for each range of mole conjugated diene per mole of palladium cation. Conveniently, the amount of catalyst system is small. The ratio of mole conjugated diene per mole of palladium cation can vary between wide limits, suitably in the range from $1 \times 10^1$ to $2 \times^7$ mole conjugated diene per mole of palladium cation, dependent of a continuous, semi-continuous or batch-wise process is being used. The use of a continuous manner of operation conveniently allows for high molar ratios near the upper limit of this range. For a batch-wise process, suitable the ratio of mole conjugated diene per mole of palladium cation is in the range of $2 \times 10^2$ to $2 \times 10^6$ more suitably in the range of $3 \times 10^2$ to $2 \times 10^5$.

In the process of the invention liquid carbonylation product and/or surplus of a carbonylation reactant such as conjugated diene or hydroxyl group containing compound may serve as solvent during the reaction. It is also possible to perform the reaction in the presence of an extra inert solvent. Suitable extra inert solvents are for example polar, aprotic compounds, such as ketones, ethers, e.g. anisole, tetrahydrofuran or the dimethylether of diethyleneglycol, or sulphones, e.g. sulpholane.

The carbonylation reaction is conveniently carried out at moderate temperatures, generally ranging from 20 to 200° C., preferably ranging from 80 to 180° C.

The invention is also directed to a catalyst system and its use as a homogeneous catalyst, based on:

(a) a source of palladium cations,
(b) a phosphorus-containing ligand,
(c) a source of anions, wherein the phosphorus-containing ligand is a ligand having the general formula I $$X^1—R—X^2 \qquad (I)$$

wherein $X^1$ and $X^2$ represent a cyclic group with at least 5 ring atoms, of which one is a phosphorus atom, and R represents a bivalent organic bridging group, connecting both phosphorus atoms, containing from 1 to 4 atoms in the bridge and wherein one or both cyclic groups $X^1$ and $X^2$ are substituted with one or more alkyl groups having from 1 to 4 carbon atoms.

Preferred embodiments of the catalyst system are the same as those described hereinbefore. The above catalyst is preferably used as a carbonylation catalyst.

The invention will be illustrated by the following non-limiting examples.

EXAMPLE 1

A 300 ml magnetically stirred Hastelloy C autoclave (Hastelloy is a Trade Mark) was filled with 40 ml methanol, 40 ml solvent, 0.5 mmol palladium acetate, 0.6 mmol 1,2-P,P'bis(9-phosphabicyclononyl)ethane (mainly the symmetrical [3,3,1] isomer) and 2 mmol 2,6-dimethoxybenzoic acid. As used anisole was used, which is a non-polar solvent with solvent properties similar to that of esters. Subsequently the autoclave was closed, evacuated and hereafter 20 ml (circa 230 mmol) of 1,3-butadiene was added, thus obtaining a ratio of about 460:1 mole conjugated diene per mole of palladium cation, and carbon monoxide to an initial carbon monoxide pressure of 40 bar was added. The autoclave was heated to 170° C. After a residence time of 10 hours, the contents of the autoclave were analysed by means of gas-liquid chromatography. The initial rate of carbonylation was 240 mol CO/grams atom palladium/hour. The initial rate of carbonylation was defined as the mean rate of carbon monoxide consumption over the first 30% butadiene conversion. The total selectivity to butadiene carbonylation products was found to be more than 95%. The butadiene carbonylation products consisted of 13% pentenoates and 87% diesters. The diesters consisted of 59% dimethyladipate, 19% dimethyl 2-methyl glutarate, 9% dimethyl 2-ethyl succinate glutarate and 13% dimethyl propyl maleate. Traces of vinylcyclohexene and its carbonylation products were formed.

EXAMPLE 2

Example 1 was repeated, except that instead of 2 mmol 2,6-dimethoxybenzoic acid, 5 mmol 3-pentenoic acid was used as a source of anions. After a residence time of 10 hours, the contents of the autoclave were analysed. The initial rate of carbonylation was 400 mol CO/grams atom palladium/hour. The total selectivity to butadiene carbonylation products was found to be 90%. The butadiene carbonylation products consisted of 57% pentenoates and 43% diesters.

Comparative Experiment A

Example 1 was repeated, except that instead of 0.6 mmol 1,2-P,P'bis(9-phosphabicyclononyl)ethane, 0.6 mmol 1,2-P,P'bis(dicyclohexylphosphine)ethane was used as a phosphorus containing ligand. After a residence time of 10 hours, the contents of the autoclave were analysed. The initial rate of carbonylation was only 60 mol CO/grams atom palladium/hour, only a quarter of the initial rate of example 1. The total selectivity to butadiene carbonylation products was found to be less than 60%. The butadiene carbonylation products consisted of 95% pentenoates and 5% diesters.

EXAMPLE 3

Example 1 was repeated, except that instead of 2 mmol 2,6-dimethoxybenzoic acid, 5 mmol 2,6-dimethoxybenzoic acid was used as a source of anions. After a residence time of 5 hours, the contents of the autoclave were analysed. The initial rate of carbonylation was 350 mol CO/grams atom palladium/hour. The total selectivity to butadiene carbonylation products was found to be more than 95%. The butadiene carbonylation products consisted of 87% pentenoates and 13% diesters.

EXAMPLE 4

Example 1 was repeated, except that the autoclave was filled with 20 ml methanol, 40 ml anisole, 0.5 mmol palladium acetate, 0.6 mmol 1,2-P,P'bis(1,5-dimethyl, 9-phosphabicyclononyl)ethane (mainly the symmetrical [3,3,1] isomer), 10 mmol 3-pentenoic acid, closed and evacuated. Hereafter 20 ml of 1,3-butadiene and carbon monoxide to an initial carbon monoxide pressure of 40 bar was added. The autoclave was heated to 150° C. After a residence time of 5 hours, the contents of the autoclave were analysed. The initial rate of carbonylation was 300 mol CO/grams atom palladium/hour. The total selectivity to butadiene carbonylation products was found to be more than 95%. The butadiene carbonylation products consisted of 92% pentenoates and 8% diesters.

EXAMPLE 5

Example 1 was repeated except that the autoclave was filled with 20 ml methanol, 40 ml anisole, 0.5 mmol palladium acetate, 0.6 mmol 1,2-P,P'bis(9-phosphabicyclononyl) orthoxylene, 10 mmol 2,4,6-trimethylbenzoic acid, closed and evacuated. Hereafter 20 ml of 1,3-butadiene and carbon monoxide to an initial carbon monoxide pressure of 40 bar was added. The autoclave was heated to 150° C. After a residence time of 5 hours, the contents of the autoclave were analysed. The initial rate of carbonylation was 100 mol CO/grams atom palladium/hour. The total selectivity to butadiene carbonylation products was found to be 95%. The butadiene carbonylation products consisted of 99% pentenoates and 1% diesters.

Comparative Experiment B

This experiment is comparable to the examples given in U.S. Patent Specification No. 5,495,041. Example 1 was repeated, except that the autoclave was filled with 20 ml methanol, 40 ml anisole, 0.5 mmol palladium acetate, 1.0 mmol 1,4-P,P'bis(diphenylphosphine)butane, 10 mmol 3-pentenoic acid, closed and evacuated. Hereafter 20 ml of 1,3-butadiene and carbon monoxide to an initial carbon monoxide pressure of 40 bar was added. The autoclave was heated to 150° C. After a residence time of 5hours, the contents of the autoclave were analysed. The initial rate of carbonylation was only 70 mol CO/grams atom palladium/hour. The total selectivity to butadiene carbonylation products was found to 95%. The butadiene carbonylation products consisted of 98% pentenoates and 2% diesters.

Comparative Experiment C

Comparative experiment B was repeated, except that instead of 1.0 mmol 1,4-P,P'bis(diphenylphosphine)butane, 0.6 mmol 1,4-P,P'bis(diphenylphosphine)butane was used. After a residence time of 5 hours, the contents of the autoclave were analysed. The initial rate of carbonylation was only 20 mol CO/grams atom palladium/hour.

Comparative Experiment D

Comparative experiment C was repeated, except that instead of 0.6 mmol 1,4-P,P'bis(diphenylphosphine)butane, 0.6 mmol 1,2-P,P'bis(diphenylphosphine)ethane was used. The reaction rate was less than 20 mol CO/grams atom Palladium/hour.

Comparative Experiment E

Comparative experiment D was repeated, except that instead of 0.6 mmol 1,2-P,P'bis(diphenylphosphine)ethane, 1.0 mmol 1,2-P,P'bis(diphenylphosphine)ethane was used. After a residence time of 5 hours, the contents of the autoclave were analysed. The initial rate of carbonylation was 40 mol CO /grams atom palladium/hour. The total selectivity to butadiene carbonylation products was found to be 60%. The butadiene carbonylation products consisted of 80% pentenoates and 20% diesters.

Comparative Experiment F

Comparative experiment E was repeated, except that instead of 1.0 mmol 1,2—P,P'bis(diphenylphosphine)ethane, 0.6 mmol 1,2-P,P'bis(ditert-butylphosphine)ethane was used. After a residence time of 5 hours, the contents of the autoclave were analysed. The initial rate of carbonylation was only 30 mol CO/grams atom palladium/hour. The total selectivity to butadiene carbonylation products was found to be 55%. The butadiene carbonylation products consisted of 90% pentenoates and 10% diesters.

In Table I the phosphorus-containing ligands, the sources of anions and the quantities of methanol, phosphorus-containing ligand and source of anions are stated for each example. The autoclave temperatures and the residence times are also stated in Table I. Furthermore the results of each example are summarized in Table I. From the results of the examples it can be concluded that surprisingly the use of the substituted or non-substituted phosphorus-containing ligands according to the invention renders the catalyst system much more active than the conventionally used phosphorus-containing ligands. As illustrated by comparing comparative examples A–F with examples 1–5, the initial rate of carbonylation can be more than doubled, while still obtaining high selectivities. The use of the substituted phosphorus containing ligand of example 4 is especially advantageous since here a very high initial rate of carbonylation in combination with a very high selectivity to carbonylation and a very high ratio of mono- to diesters is obtained.

TABLE I

| | Catalyst system (apart from palladium cations) | | | |
|---|---|---|---|---|
| Example | Phosphorus-containing ligand | mmol | source of anions | mmol |
| 1 | 1,2-P,P'bis(9-phosphabicyclononyl)ethane | 0.6 | 2,6-dimethoxybenzoic acid | 2 |
| 2 | 1,2-P,P'bis(9-phosphabicyclononyl)ethane | 0.6 | 3-pentenoic acid | 5 |
| A | 1,2-P,P'bis(dicyclohexylphosphine)ethane | 0.6 | 2,6-dimethoxybenzoic acid | 2 |
| 3 | 1,2-P,P'bis(9-phosphabicyclononyl)ethane | 0.6 | 2,6-dimethoxybenzoic acid | 5 |
| 4 | 1,2-P,P'bis(1,5-dimethyl, 9-phosphabicyclononyl)ethane | 0.6 | 3-pentenoic acid | 10 |
| 5 | P,P'bis(9-phosphabicyclononyl)orthoxylene | 0.6 | 2,4,6-trimethylbenzoic acid | 10 |
| B | 1,4-P,P'bis(diphenylphosphine)butane | 1.0 | 3-pentenoic acid | 10 |
| C | 1,4-P,P'bis(diphenylphosphine)butane | 0.6 | 3-pentenoic acid | 10 |
| D | 1,2-P,P'bis(diphenylphosphine)ethane | 0.6 | 3-pentenoic acid | 10 |
| E | 1,2-P,P'bis(diphenylphosphine)ethane | 1.0 | 3-pentenoic acid | 10 |
| F | 1,2-P,P'bis(ditert-butylphosphine)ethane | 0.6 | 3-pentenoic acid | 10 |

TABLE I-continued

| Example | Methanol (ml) | Temperature (° C.) | Residence Time (hr) | Initial Rate of Carbonylation (mol CO/gram atom Pd/hr) | Selectivity to carbonylation (%) | Ratio mono-: diesters |
|---|---|---|---|---|---|---|
| 1 | 40 | 170 | 10 | 240 | >95 | 13:87 |
| 2 | 40 | 170 | 10 | 400 | 90 | 57:43 |
| A | 40 | 170 | 10 | 60 | <60 | 95:5 |
| 3 | 40 | 170 | 5 | 350 | >95 | 87:13 |
| 4 | 20 | 150 | 5 | 300 | >95 | 92:8 |
| 5 | 20 | 150 | 5 | 100 | 95 | 99:1 |
| B | 20 | 150 | 5 | 70 | 95 | 98:2 |
| C | 20 | 150 | 5 | 20 | — | — |
| D | 20 | 150 | — | <20 | — | — |
| E | 20 | 150 | 5 | 40 | 60 | 80:20 |
| F | 20 | 150 | 5 | 30 | 55 | 90:10 |

What is claimed is:

1. A process for the carbonylation of conjugated dienes, whereby a conjugated diene is reacted with carbon monoxide and a hydroxyl group containing compound selected from the group consisting of alkanols and alkane diols in the presence of a catalyst system including:

(a) a palladium salt,
   (b) a phosphorus-containing ligand,
   (c) a protonic acid having a pKa value of greater than 1, wherein the phosphorus-containing ligand is a ligand having the general formula I

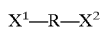 (I)

wherein $X^1$ and $X^2$ represent a substituted or non-substituted cyclic group with at least 5 ring atoms, of which one is a phosphorus atom and the rest are carbon atoms, wherein the substitution, if any, is provided by one or more hydrocarbyl groups containing carbon atoms and/or hetero atoms, and R represents a bivalent organic bridging group, connecting both phosphorus atoms, containing 2 or 3 carbon atoms in the bridge; and wherein the molar ratio of conjugated diene to palladium cation is at least 300:1.

2. A process as claimed in claim 1, wherein the conjugated diene is 1,3-butadiene.

3. A process as claimed claim 1, wherein the hydroxyl group containing compound is an alkanol with from 1 to 20 carbon atoms per molecule.

4. A process as claimed in claim 1, wherein component (b) of the catalyst system is a phosphorus-containing ligand of formula (I), wherein the bivalent organic bridging group R is an ethylene or a propylene group connected via their terminal carbon atoms to the respective phosphorus atoms of $X^1$ and $X^2$.

5. A process as claimed in claim 1, wherein $X^1$ and $X^2$ represent a substituted or non-substituted bicyclic group with at least 5 ring atoms, of which one is a phosphorus atom and the rest are carbon atoms.

6. A process as claimed in claim 5, wherein $X^1$ and $X^2$ represent a substituted or non-substituted or 9-phosphabicyclononyl group wherein the substitution, if any, is provided by hydrocarbyl groups containing carbon atoms and/or hetero atoms.

7. A process as claimed in claim 6, wherein one or both of the phosphabicylononyl groups is substituted with one or more alkyl groups having from 1 to 4 carbon atoms.

8. A process as claimed in claim 1, wherein the protonic acid is selected from the group consisting of sulphuric acid, phosphoric acid, and carboxylic acids.

9. A process as claimed in claim 1, wherein 1,3-butadiene is converted into methyl pentenoate.

10. A process to prepare ε-caprolactam wherein methylpentenoate prepared according to the process of claim 1 is hydroformylated to methyl formylvalerate which is subjected to reductive amination and cyclisation to form ε-caprolactam.

11. The process of claim 1 wherein the conjugated diene is selected from the group consisting of conjugated dienes having from 4 to 20 carbon atoms per molecule.

12. The process of claim 11 wherein the conjugated diene is selected from the group consisting of conjugated dienes having from 4 to 8 carbon atoms per molecule.

13. The process of claim 1 wherein the alkanol has from 1 to 20 carbon atoms per molecule and the alkane diol has from 2 to 20 carbon atoms per molecule.

14. The process of claim 13 wherein the alkanol contains from 1 to 6 carbon atoms per molecule and the alkane diol contains from 2 to 6 carbon atoms per molecule.

15. The process of claim 1 wherein the palladium salt is a carboxylic acid palladium salt.

16. The process of claim 15 wherein the carboxylic acid palladium salt contains up to 10 carbon atoms.

17. The process of claim 8 wherein the protonic acid is a carboxylic acid.

18. The process of claim 17 wherein the carboxylic acid is a benzoic acid.

19. The process of claim 18 wherein the benzoic acid is substituted with a substituent selected from the group consisting of halide groups, hydrocarbyl groups, carboxy groups, and alkoxy groups.

20. The process of claim 19 wherein the substituents are selected from the group consisting of methyl and methoxy groups.

* * * * *